US 6,635,635 B2

(12) United States Patent
Cordi et al.

(10) Patent No.: US 6,635,635 B2
(45) Date of Patent: Oct. 21, 2003

(54) BENZOTHIADIAZINE COMPOUNDS

(75) Inventors: Alex Cordi, Suresnes (FR); Patrice Desos, Courbevoie (FR); François Lefoulon, Orleans (FR); Pierre Lestage, La Celle Saint Cloud (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/916,479

(22) Filed: Jul. 27, 2001

(65) Prior Publication Data
US 2002/0037894 A1 Mar. 28, 2002

(30) Foreign Application Priority Data
Jul. 28, 2000 (FR) .............................................. 00 09916

(51) Int. Cl.⁷ ........................ C07D 513/04; A01N 43/88
(52) U.S. Cl. ......................................... 514/222.8; 544/9
(58) Field of Search ............................ 514/222.8; 544/9

(56) References Cited
U.S. PATENT DOCUMENTS
3,316,238 A * 4/1967 Hanke et al. .................... 544/9

* cited by examiner

Primary Examiner—John M. Ford
(74) Attorney, Agent, or Firm—The Firm of Hueschen and Sage

(57) ABSTRACT

Compound of formula (I):

wherein:

$R_1$ represents hydroxy, RCO—O— or RCO—$NR_a$—, $R_2$ represents hydrogen, halogen, or hydroxy, R'CO—O or R'CO—$NR'_a$—, R and R', which may be identical or different, represent linear or branched ($C_1$–$C_6$)alkyl optionally substituted by aryl, linear or branched ($C_2$–$C_6$)alkenyl optionally substituted by aryl, linear or branched ($C_1$–$C_6$) perhaloalkyl, ($C_3$–$C_7$)cycloalkyl, adamantyl, aryl or heteroaryl, $R_a$ and $R'_a$, which may be identical or different, represent hydrogen or linear or branched ($C_1$–$C_6$)alkyl, linear or branched ($C_1$–$C_6$)perhaloalkyl, linear or branched ($C_1$–$C_6$)acyl, aryl or heteroaryl, its isomer and addition salts thereof with a pharmaceutically acceptable acid or base and medicinal products containing the same are useful as AMPA modulators.

7 Claims, No Drawings

BENZOTHIADIAZINE COMPOUNDS

BACKGROUND OF THE INVENTION

It is now recognised that excitatory amino acids and more especially glutamate play a key role in the physiological processes of neuronal plasticity and in the mechanisms underlying learning and memory. Pathophysiological studies have clearly indicated that a deficit in glutamatergic neurotransmission is closely associated with the development of Alzheimer's disease (Neuroscience and Biobehavioral reviews, 1992, 16, 13–24; Progress in Neurobiology, 1992, 39, 517–545).

Moreover, countless studies over recent years have shown the existence of excitatory amino acid receptor sub-types and of their functional interactions (Molecular Neuropharmacology, 1992, 2, 15–31).

Among those receptors, the AMPA receptor ("α-amino-3-hydroxy-5-methyl-4-isoxazole-propionic acid") seems to be the most implicated in the phenomena of physiological neuronal excitability and especially in those phenomena implicated in the processes of memorisation. For example, learning has been shown to be associated with an increase in AMPA binding to its receptor in the hippocampus, one of the cerebral regions essential to mnemocognitive processes. Similarly, nootropic agents, such as aniracetam, have very recently been described as modulating positively the AMPA receptors of neuronal cells (Journal of Neurochemistry, 1992, 58, 1199–1204).

DESCRIPTION OF THE PRIOR ART

In the literature, compounds of benzamide structure have been described as having that same mechanism of action and as improving mnesic performance (Synapse, 1993, 15, 326–329). Compound BA 74, in particular, is the most active of those new pharmacological agents.

Finally, Patent Specification EP 692 484 describes a benzothiadiazine compound having a facilitatory action on the AMPA flux and Patent Application WO 99/42456 describes, inter alia, a number of benzothiadiazine compounds as AMPA receptor modulators.

In addition to being new, the benzothiadiazine compounds that are the subject-matter of the present invention, surprisingly, have pharmacological activity on the AMPA flux that is clearly superior to that of the compounds of similar structure described in the prior art. They are useful as AMPA modulators in the treatment or prevention of mnemocognitive disorders associated with age, anxiety or depression syndromes, progressive neurogenerative disorders, Alzheimer's disease, Pick's disease, Huntington's chorea, schizophrenia, sequelae of acute neurodegenerative disorders, sequelae of ischaemia and with sequelae of epilepsy.

DETAILED DESCRIPTION OF THE INVENTION

More specifically, the present invention relates to compounds of formula (I):

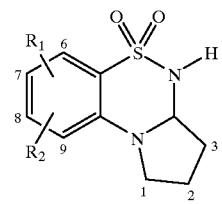

wherein:
$R_1$ represents a hydroxy, RCO—O— or RCO—$NR_a$— group,
$R_2$ represents a hydrogen atom, a halogen atom, or a hydroxy, R'CO—O or R'CO—$NR'_a$— group,
R and R', which may be identical or different, represent a linear or branched ($C_1$–$C_6$)alkyl group optionally substituted by an aryl group, a linear or branched ($C_2$–$C_6$) alkenyl group optionally substituted by an aryl group, a linear or branched ($C_1$–$C_6$)perhaloalkyl group, a ($C_3$–$C_7$)cycloalkyl group, an adamantyl group, an aryl group or a heteroaryl group,
$R_a$ and $R'_a$, which may be identical or different, represent a hydrogen atom or a linear or branched ($C_1$–$C_6$)alkyl group, a linear or branched ($C_1$–$C_6$)perhaloalkyl group, a linear or branched ($C_1$–$C_6$)acyl group, an aryl group or a heteroaryl group,
their isomers and addition salts thereof with a pharmaceutically acceptable acid or base, it being understood that:
"aryl group" is understood to mean a monocyclic aromatic group or a bicyclic group in which at least one of the rings is aromatic, which groups are optionally substituted by one or more, identical or different, groups selected from halogen, linear or branched ($C_1$–$C_6$)alkyl, linear or branched ($C_1$–$C_6$)alkoxy, linear or branched ($C_1$–$C_6$)perhaloalkyl, linear or branched ($C_1$–$C_6$)perhaloalkoxy, hydroxy, cyano, nitro, amino (optionally substituted by one or more linear or branched ($C_1$–$C_6$)alkyl groups), aminosulphonyl (optionally substituted by one or more linear or branched ($C_1$–$C_6$)alkyl groups) and phenyl (optionally substituted by one or more, identical or different, groups selected from halogen, linear or branched ($C_1$–$C_6$)alkyl, linear or branched ($C_1$–$C_6$)perhaloalkyl, hydroxy and linear or branched ($C_1$–$C_6$)alkoxy),
"heteroaryl group" is understood to mean a monocyclic aromatic group or a bicyclic group in which at least one of the rings is aromatic, which groups contain one, two or three identical or different hetero atoms selected from nitrogen, oxygen and sulphur, and are optionally substituted by one or more, identical or different, groups selected from halogen, linear or branched ($C_1$–$C_6$)alkyl, linear or branched ($C_1$–$C_6$)alkoxy, linear or branched ($C_1$–$C_6$)perhaloalkyl, linear or branched ($C_1$–$C_6$)perhaloalkoxy, hydroxy, cyano, nitro, amino (optionally substituted by one or more linear or branched ($C_1$–$C_6$)-alkyl groups) and aminosulphonyl (optionally substituted by one or more linear or branched ($C_1$–$C_6$)alkyl groups).
Among the pharmaceutically acceptable acids, there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases, there may be mentioned by way of non-limiting example sodium hydroxide, potassium hydroxide, triethylamine, tert-butylamine, etc.

The preferred aryl groups are the optionally substituted phenyl, naphthyl and tetrahydronaphthyl groups.

The preferred heteroaryl groups are the optionally substituted pyridyl, pyrrolyl, thienyl, furyl, imidazolyl and indolyl groups and more especially the groups pyridyl, thienyl and furyl.

Some preferred compounds of the invention are the compounds of formula (I) wherein $R_1$ represents a hydroxy group and $R_2$ represents a hydrogen or halogen atom.

Other preferred compounds of the invention are the compounds of formula (I) wherein $R_1$ represents an RCO—O group and $R_2$ represents a hydrogen atom. Among the compounds of the invention, when $R_1$ represents an RCO—O group and $R_2$ represents a hydrogen atom, the R group is preferably a $(C_3-C_7)$cycloalkyl group, an aryl group or a heteroaryl group.

The substituent $R_1$ of the compounds of formula (I) is preferably in the 7-position.

The preferred compounds of the invention are:
5,5-dioxo-2,3,3a,4-tetrahydro-1H-pyrrolo[2,1-c][1,2,4]benzothiadiazin-7-ol
5,5-dioxo-2,3,3a,4-tetrahydro-1H-pyrrolo[2,1-c][1,2,4]benzothiadiazin-7-yl benzoate
5,5-dioxo-2,3,3a,4-tetrahydro-1H-pyrrolo[2,1-c][1,2,4]benzothiadiazin-7-yl cyclohexane-carboxylate
5,5-dioxo-2,3,3a,4-tetrahydro-1H-pyrrolo[2,1-c][1,2,4]benzothiadiazin-7-yl cyclobutane-carboxylate
5,5-dioxo-2,3,3a,4-tetrahydro-1H-pyrrolo[2,1-c][1,2,4]benzothiadiazin-7-yl 4-methyl-benzoate
5,5-dioxo-2,3,3a,4-tetrahydro-1H-pyrrolo[2,1-c][1,2,4]benzothiadiazin-7-yl 3-thiophene-carboxylate
5,5-dioxo-2,3,3a,4-tetrahydro-1H-pyrrolo[2,1-c][1,2,4]benzothiadiazin-7-yl 2-thiophene-carboxylate
5,5-dioxo-2,3,3a,4-tetrahydro-1H-pyrrolo[2,1-c][1,2,4]benzothiadiazin-7-yl 3-furan-carboxylate
5,5-dioxo-2,3,3a,4-tetrahydro-1H-pyrrolo[2,1-c][1,2,4]benzothiadiazin-7-yl 2-furan-carboxylate
5,5-dioxo-2,3,3a,4-tetrahydro-1H-pyrrolo[2,1-c][1,2,4]benzothiadiazin-7-yl nicotinate.

The invention relates also to a process for the preparation of compounds of formula (I), characterised in that there is used as starting material a compound of formula (II):

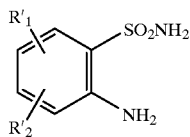

(II)

wherein:

$R'_1$ represents a linear or branched $(C_1-C_6)$alkoxy group, or a nitro group, $R'_2$ represents a hydrogen atom, a halogen atom, a linear or branched $(C_1-C_6)$alkoxy group, or a nitro group, which is reacted with the acid chloride of formula (III) in the presence of a base, in a tetrahydrofuran or acetonitrile medium:

to yield a compound of formula (IV):

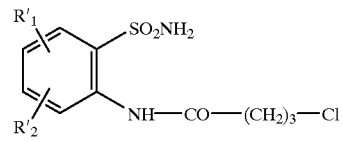

(IV)

wherein $R'_1$ and $R'_2$ are as defined hereinbefore, which is then cyclised in a basic medium, to yield a compound of formula (V):

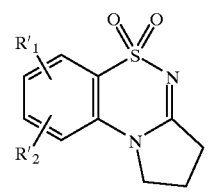

(V)

wherein $R'_1$, and $R'_2$ are as defined hereinbefore, which is subjected to reduction, in an alcoholic medium or in a dimethylformamide medium, in the presence of sodium borohydride, to yield a compound of formula (VI):

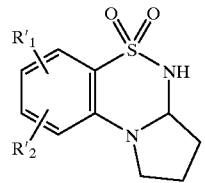

(VI)

wherein $R'_1$ and $R'_2$ are as defined hereinbefore, which compound of formula (VI):

when $R'_1$ represents a linear or branched $(C_1-C_6)$alkoxy group, is subjected to the action of boron tribromide, to yield:
  either the compound of formula (I/a), a particular case of the compounds of formula (I):

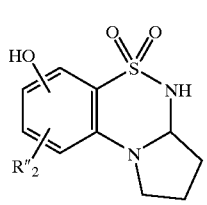

(I/a)

wherein $R''_2$ represents a hydrogen atom, a halogen atom or a hydroxy group, or the compound of formula (VII):

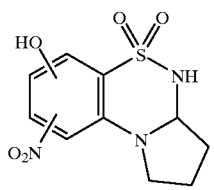

(VII)

which is then subjected to reduction, to yield the corresponding amine, which is optionally substituted, and then subjected to one or two successive acylations, to yield the compound of formula (I/b), a particular case of the compounds of formula (I):

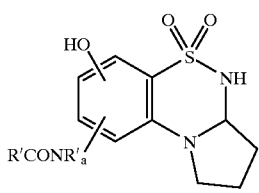

(I/b)

wherein R' and R'$_a$ are as defined for formula (I),
when R'$_1$ represents a nitro group, is subjected to reduction to yield the corresponding amine, which is optionally substituted, and then to an acylation, to yield the compound of formula (I/c):

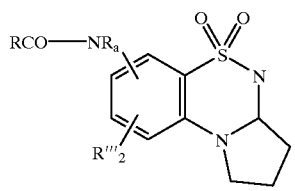

(I/c)

wherein R and R$_a$ are as defined hereinbefore, and R'''$_2$ represents a hydrogen atom, a halogen atom, a hydroxy group or an R'CONR'$_a$ group wherein R' and R'$_a$ are as defined for formula (I),
wherein the hydroxy function(s) present in the compounds of formulae (I/a), (I/b) and (I/c) may be acylated to yield the compounds (I/d) wherein the hydroxy group(s) of the phenyl ring has/have been converted to R—CO—O or R'—CO—O— groups wherein R and R' are as defined for formula (I), which compounds (I/a) to (I/d) constitute the totality of the compounds of formula (I), which are purified, if necessary, according to a conventional purification technique, are separated, where appropriate, into their isomers according to a conventional separation technique, and converted, if desired, into addition salts thereof with a pharmaceutically acceptable acid or base.

The invention relates also to pharmaceutical compositions comprising as active ingredient a compound of formula (I) with one or more suitable, inert, non-toxic excipients. Among the pharmaceutical compositions according to the invention, there may be mentioned more especially those that are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions, etc.

The useful dosage can be adapted to the nature and severity of the disorder, the route of administration and the age and weight of the patient. The dosage varies from 1 to 500 mg per day in one or more administrations.

The following Examples illustrate the invention but do not limit it in any way.

The starting materials used are known products or are prepared according to known procedures.

The structures of the compounds described in the Examples were determined according to the usual spectrophotometric techniques (infrared, NMR, mass spectrometry, etc.).

EXAMPLE 1

5,5-Dioxo-2,3,3a,4-tetrahydro-1H-pyrrolo[2,1-c][1,2,4]benzothiadiazin-7-ol

Step A: N-[2-(Aminosulphonyl)-4-methoxyphenyl]-4-chlorobutanamide 144 mmol of triethylamine are added to a solution containing 96.4 mmol of 2-amino-5-methoxybenzenesulphonamide in 200 ml of tetrahydrofuran (THF), followed dropwise by a solution containing 135 mmol of 4-chlorobutanoic acid chloride in 30 ml of THF. After stirring overnight at room temperature, the THF is removed by evaporation and the residue is taken up in water. After extraction with ethyl acetate, the organic phase is washed and dried. After evaporation, the expected product is obtained in the form of an oil.

Step B: 5,5-Dioxo-7-methoxy-2,3-dihydro-1H-pyrrolo[2,1-c]-[1,2,4]benzothiadiazine The product obtained in the preceding Step is stirred overnight, at room temperature, in 320 ml of an aqueous 1N sodium hydroxide solution. After the addition of 50 ml of ethyl acetate and vigorous stirring, the expected product precipitates and is filtered off, rinsed and dried.

Elemental microanalysis:

|  | C % | H % | N % | S % |
|---|---|---|---|---|
| calculated | 52.37 | 4.79 | 11.10 | 12.71 |
| found | 52.30 | 4.79 | 10.98 | 12.96 |

Step C: 5,5-Dioxo-7-methoxy-2,3,3a,4-tetrahydro-1H-pyrrolo[2,1-c][1,2,4]-benzothiadiazine 106.5 mmol of sodium borohydride are added to a suspension containing 35.5 mmol of the product obtained in the preceding Step in 40 ml of dimethylformamide (DMF). After stirring overnight at room temperature, the reaction mixture is cooled and then 150 ml of an ice-cold solution of 1 N hydrochloric acid are added to the preceding mixture. The expected product precipitates and is filtered off.

Melting point: 193–198° C.

Elemental microanalysis:

|  | C % | H % | N % | S % |
|---|---|---|---|---|
| calculated | 51.95 | 5.55 | 11.02 | 12.61 |
| found | 51.60 | 5.59 | 10.87 | 12.69 |

Step D: 5,5-Dioxo-2,3,3a,4-tetrahydro-1H-pyrrolo[2,1-c][1,2,4]benzothiadiazin-7-ol 79.3 mmol of boron tribromide are added dropwise to a suspension, maintained at −60° C. under nitrogen, containing 26.7 mmol of the product obtained in the preceding Step in 350 ml of dichloromethane. The temperature is maintained for one hour and then the whole returns to room temperature and is stirred overnight. After cooling of the reaction mixture in an ice-bath, 100 ml of water are added and the two-phase system that forms is stirred vigorously. The resulting suspension is filtered. The white solid obtained is washed with water and with ether and dried to yield the expected product.

Melting point: 237–242° C.
Elemental microanalysis:

|  | C % | H % | N % | S % |
|---|---|---|---|---|
| calculated | 49.99 | 5.03 | 11.66 | 13.34 |
| found | 49.82 | 5.17 | 11.44 | 13.64 |

Examples 2 to 4 were obtained according to the process described in Example 1 using corresponding starting materials.

EXAMPLE 2

5,5-Dioxo-2,3a,4-tetrahydro-1H-pyrrolo[2,1-c][1,2,4]benzothiadiazin-6-ol

In Step A, 2-amino-5-methoxybenzenesulphonamide is replaced by 2-amino-6-methoxybenzenesulphonamide.

Melting point: >300° C.
Elemental microanalysis:

|  | C % | H % | N % | S % |
|---|---|---|---|---|
| calculated | 49.99 | 5.03 | 11.66 | 13.34 |
| found | 49.75 | 4.88 | 11.29 | 13.51 |

EXAMPLE 3

5,5-Dioxo-2,3,3a,4-tetrahydro-1H-pyrrolo[2,1-c][1,2,4]benzothiadiazin-8-ol

In Step A, 2-amino-5-methoxybenzenesulphonamide is replaced by 2-amino-4-methoxybenzenesulphonamide.

Melting point: >260° C.
Elemental microanalysis:

|  | C % | H % | N % | S % |
|---|---|---|---|---|
| calculated | 49.99 | 5.03 | 11.66 | 13.34 |
| found | 49.31 | 5.03 | 11.17 | 13.45 |

EXAMPLE 4

5,5-Dioxo-8-fluoro-2,3,3a,4-tetrahydro-1H-pyrrolo[2,1-c][1,2,4]-benzothiadiazin-7-ol In Step A, 2-amino-5-methoxybenzenesulphonamide is replaced by 2-amino-4-fluoro-5-methoxybenzenesulphonamide.

Melting point: 173–177° C.

Elemental microanalysis:

|  | C % | H % | N % | S % |
|---|---|---|---|---|
| calculated | 46.51 | 4.29 | 10.85 | 12.41 |
| found | 46.35 | 4.41 | 10.62 | 11.72 |

EXAMPLE 5

5,5-Dioxo-9-fluoro-2,3,3a,4-tetrahydro-1H-pyrrolo[2,1-c][1,2,4]-benzothiadiazin-7-ol Step A: N-[2-(Aminosulphonyl)-4-methoxy-6-fluorophenyl]-4-chlorobutanamide 2-Amino-5-methoxybenzenesulphonamide is replaced by 2-amino-3-fluoro-5-methoxybenzenesulphonamide in Step A of Example 1.

Step B: 3-Fluoro-5-methoxy-2-(2-oxopyrrolidin-1-yl)benzenesulphonamide

The expected product is obtained under the conditions described in Step B of Example 1 starting from the compound described in the preceding Step. Melting point: 205° C.

Step C: 5,5-Dioxo-9-fluoro-7-methoxy-2,3-dihydro-1H-pyrrolo[2,1-c][X1,2,4]-benzothiadiazine 9.5 mmol of 1,8-diazabicyclo[5,4,0]undec-7-ene are added to 4.75 mmol of the product described in the preceding Step in 20 ml of THF. The whole is refluxed for 5 hours with stirring. After dilution with water, the precipitate that forms is filtered off, washed with water and dried to yield the expected product.

Melting point: 215° C.

Step D: 5,5-Dioxo-9-fluoro-7-methoxy-2,3,3a,4-tetrahydro-1H-pyrrolo[2,1-c]-[1,2,4]benzothiadiazine The expected product is obtained according to the process described in Step C of Example 1 starting from the compound obtained in the preceding Step.

Melting point: 145° C.

Step E: 5,5-Dioxo-9-fluoro-2,3,3a,4-tetrahydro-1H-pyrrolo[2,1-c][1,2,4]-benzothiadiazin-7-ol The expected product is obtained according to the process described in Step D of Example 1 starting from the compound obtained in the preceding Step.

Melting point: 167–169° C.
Elemental microanalysis:

|  | C % | H % | N % | S % |
|---|---|---|---|---|
| calculated | 46.51 | 4.29 | 10.85 | 12.41 |
| found | 46.55 | 4.41 | 10.57 | 12.34 |

EXAMPLE 6

5,5-Dioxo-2,3, 3a,4-tetrahydro-1H-pyrrolo[2,1-c][1,2,4]benzothiadiazin-9-ol

The expected product is obtained according to the process described in Example 5, in Step A replacing 2-amino-3-fluoro-5-methoxybenzenesulphonamide by 2-amino-3-methoxybenzenesulphonamide.

Melting point: 215–21 7° C.

Elemental microanalysis:

|  | C % | H % | N % | S % |
|---|---|---|---|---|
| calculated | 49.99 | 5.03 | 11.66 | 13.34 |
| found | 49.95 | 5.06 | 11.33 | 13.03 |

EXAMPLE 6a

5,5-Dioxo-2,3,3a,4-tetrahydro-1H-pyrrolo[2,1-c][1,2,4]benzothiadiazin-7,8-diol The expected product is obtained according to the process described in example 5, in step A replacing 2-amino-3-fluoro-5-methoxybenzenesulphonamide by 2-amino-4,5-dimethoxybenzenesulphonamide.

Melting point: >310° C.

Elemental microanalysis:

|  | C % | H % | N % | S % |
|---|---|---|---|---|
| calculated | 46.87 | 4.72 | 10.93 | 12.51 |
| found | 46.84 | 4.65 | 10.62 | 12.16 |

EXAMPLE 7

5,5-Dioxo-2,3,3a,4-tetrahydro-1H-pyrrolo[2,1c][1,2,4]benzothiadiazin-7-yl acetate 60 mg of 4-dimethylaminopyridine and 4.16 mmol of acetic anhydride are added to a suspension containing 4.16 mmol of the compound described in Example 1 in 30 ml of dichloromethane. After 20 minutes' stirring, the reaction mixture is diluted with 30 ml of dichloromethane. The organic phase is washed, dried and then evaporated. The expected product is obtained by taking up the resulting white solid in isopropyl ether and filtering.

Melting point: 163–165° C.

Elemental microanalysis:

|  | C % | H % | N % | S % |
|---|---|---|---|---|
| calculated | 51.05 | 5.00 | 9.92 | 11.36 |
| found | 51.21 | 5.06 | 9.73 | 11.43 |

EXAMPLE 8

5,5-Dioxo-2,3,3a,4-tetrahydro-1H-pyrrolo[2,1-c][1,2,4]benzothiadiazin-7-yl acetate, α isomer dextro

EXAMPLE 9

5,5-Dioxo-2,3,3a,4-tetrahydro-1H-pyrrolo[2,1-c][1,2,4]benzothiadiazin-7-yl acetate, β isomer levo The α and β isomers of the compound described in Example 7 are separated by chiral chromatography over a Chiralpak AD® column using an n-heptane/ethanol/triethylamine mixture (450/550/2) as elution solvent. After separation, each isomer is purified by chromatography over a silica column using a dichloromethane/methanol/triethylamine mixture (950/50/1) as elution solvent.

EXAMPLE 8

$[\alpha]^D_{20}$=+191.1° (c=5 mg/ml ethanol 95%)

Elemental microanalysis:

|  | C % | H % | N % | S % |
|---|---|---|---|---|
| calculated | 51.05 | 5.00 | 9.92 | 11.36 |
| found | 51.07 | 4.96 | 9.71 | 11.57 |

EXAMPLE 9

$[\alpha]^D_{20}$=−192.8° (c=5 mg/ml ethanol 95%)

Elemental microanalysis:

|  | C % | H % | N % | S % |
|---|---|---|---|---|
| calculated | 51.05 | 5.00 | 9.92 | 11.36 |
| found | 51.30 | 4.98 | 9.76 | 11.09 |

EXAMPLE 10

5,5-Dioxo-2,3,3a,4-tetrahydro-1H-pyrrolo[2,1-c][1,2,4]benzothiadiazin-7-yl pivalate 1.66 mmol of the compound of Example 1 in 40 ml of acetonitrile are stirred overnight at room temperature in the presence of 3.33 mmol of chloromethyl pivalate and a catalytic amount of dicyclohexyl-18-crown-6. The suspension is filtered and the filtrate is evaporated to dryness. The residue is taken up in dichloromethane and the organic phase is washed with a 1N hydrochloric acid solution and then with an aqueous saturated sodium chloride solution. After drying and evaporation, the resulting oily residue is crystallised from a mixture of ether/cyclohexane to yield the expected product.

Melting point: 198–202° C.

Elemental microanalysis:

|  | C % | H % | N % | S % |
|---|---|---|---|---|
| calculated | 55.54 | 6.21 | 8.64 | 9.88 |
| found | 56.01 | 6.46 | 8.36 | 9.52 |

EXAMPLE 11

5,5-Dioxo-2,3,3a,4-tetrahydro-1H-pyrrolo[2,1-c][1,2,4]benzothiadiazin-7-yl benzoate The expected product is obtained according to the process described in Example 7, replacing acetic anhydride by benzoic anhydride.

Melting point: 195° C.

Elemental microanalysis:

|  | C % | H % | N % | S % |
|---|---|---|---|---|
| calculated | 59.29 | 4.68 | 8.13 | 9.31 |
| found | 59.62 | 4.58 | 8.07 | 9.18 |

EXAMPLE 11a 5,5-Dioxo-2,3,3a,4-tetrahydro-1H-pyrrolo[2,1-c][1,2,4]benzothiadiazin-7-yl benzoate, α isomer dextro

EXAMPLE 11b 5,5-Dioxo-2,3,3a,4-tetrahydro-1H-pyrrolo[2,1-c][1,2,4]benzothiadiazin-7-yl benzoate, β isomer levo The α and β isomers of the compound described in example 11 are separated by chiral chromatography over a Whelk®01 column using isopropanol as elution solvent. After separation, each isomer is purified by chromatography over a silica column using a dichloromethane/methanol (99/1) mixture as elution solvent.

EXAMPLE 11a $[\alpha]^D_{20}$=+151,6° (C=5 mg/ml DMSO)

Elemental microanalysis:

|  | C % | H % | N % | S % |
|---|---|---|---|---|
| calculated | 59.29 | 4.68 | 8.13 | 9.31 |
| found | 59.07 | 4.69 | 8.01 | 9.16 |

EXAMPLE 12

5,5-Dioxo-2,3,3a,4-tetrahydro-1H-pyrrolo[2,1-c][1,2,4]benzothiadiazin-7-yl 4-chlorobenzoate The expected product is obtained according to the process described in Example 7, replacing acetic anhydride by p-chlorobenzoic acid chloride and adding 1.1 equivalents of triethylamine.

Melting point: 160° C.

Elemental microanalysis:

|  | C % | H % | N % | S % | Cl % |
|---|---|---|---|---|---|
| calculated | 53.90 | 3.99 | 7.39 | 8.46 | 9.36 |
| found | 53.83 | 3.95 | 7.29 | 8.57 | 9.50 |

EXAMPLE 13

N-(5,5 3-Dioxo-2,3,3a,4-tetrahydro-1H-pyrrolo[2,1-c][1,2,4]-benzothiadiazin-7-yl)benzamide Step A: 5,5-Dioxo-2,3,3a,4,-tetrahydro-1H-pyrrolo[2,1-c][1,2,4]-benzothiadiazine-7-amine 37 mmol of ammonium formate and 300 mg of 10% Pd/C are added to 3.71 mmol of 5,5-dioxo-7-nitro-2,3,3a,4,-tetrahydro-1H-pyrrolo[2,1-c][1,2,4]-benzothiadiazine suspended in 100 ml of methanol. After 90 minutes' stirring at reflux, the catalyst is filtered off while hot and rinsed with methanol. The filtrate is evaporated and the residue is taken up in water. The expected product is obtained by filtering off the precipitate.

Elemental microanalysis:

|  | C % | H % | N % | S % |
|---|---|---|---|---|
| calculated | 50.19 | 5.48 | 17.56 | 13.40 |
| found | 50.22 | 5.30 | 16.76 | 12.90 |

Step B: N-(5,5-Dioxo-2,3,3a,4-tetrahydro-1H-pyrrolo[2,1-c][1,2,4]-benzothiadiazin-7-yl)benzamide 1.32 mmol of the compound obtained in the preceding Step in 100 ml of dichloromethane are stirred overnight in the presence of 1.45 mmol of benzoic anhydride and 10 mg of 4-dimethylaminopyridine. After evaporation to dryness, the residue is taken up in a mixture of ethyl acetate/1N hydrochloric acid. After stirring, the organic phase is washed and then evaporated. The residue is taken up in ether and the expected product is obtained by filtering off the precipitate that forms.

Melting point: 293° C.

The compounds described in the following Examples were prepared by condensing the compound of Example 1 with the corresponding acid chloride in the presence of 1.5 equivalents of triethylamine and a catalytic amount of dimethylaminopyridine.

EXAMPLE 14

5,5-Dioxo-2,3,3a,4-tetrahydro-1H-pyrrolo[2,1-c][1,2,4]-benzothiadiazin-7-yl cyclohexanecarboxylate Melting point: 157° C.

Elemental microanalysis

|  | C % | H % | N % | S % |
|---|---|---|---|---|
| calculated | 58.27 | 6.33 | 7.99 | 9.15 |
| found | 58.77 | 6.47 | 8.04 | 8.93 |

EXAMPLE 15

5,5-Dioxo-2,3,3a,4-tetrahydro-1H-pyrrolo[2,1-c][1,2,4]-benzothiadiazin-7-yl adamantanecarboxylate Melting point: 199–203° C.

Elemental microanalysis

|  | C % | H % | N % | S % |
|---|---|---|---|---|
| calculated | 62.66 | 6.51 | 6.96 | 7.97 |
| found | 62.93 | 6.62 | 6.9 | 7.79 |

EXAMPLE 16

5,5-Dioxo-2,3,3a,4-tetrahydro-1H-pyrrolo[2,1-c][1,2,4]-benzothiadiazin-7-yl cyclopentanecarboxylate Melting point: 148–150° C.

Elemental microanalysis

|  | C % | H % | N % | S % |
|---|---|---|---|---|
| calculated | 57.13 | 5.99 | 8.33 | 9.53 |
| found | 57.41 | 6.02 | 8.21 | 9.11 |

EXAMPLE 17

5,5-Dioxo-2,3,3a,4-tetrahydro-1H-pyrrolo[2,1-c][1,2,4]-benzothiadiazin-7-yl cyclobutanecarboxylate Melting point: 166–170° C.

Elemental microanalysis

|  | C % | H % | N % | S % |
|---|---|---|---|---|
| calculated | 55.89 | 5.63 | 8.69 | 9.95 |
| found | 55.97 | 5.7 | 8.54 | 9.92 |

EXAMPLE 18

5,5-Dioxo-2,3,3a,4-tetrahydro-1H-pyrrolo[2,1-c][1,2,4]-benzothiadiazin-7-yl cyclopropanecarboxylate Melting point: 169–171° C.

Elemental microanalysis

|  | C % | H % | N % | S % |
|---|---|---|---|---|
| calculated | 54.53 | 5.23 | 9.08 | 10.40 |
| found | 54.58 | 5.30 | 8.70 | 10.38 |

EXAMPLE 19

5,5-Dioxo-2,3,3a,4-tetrahydro,-1H-pyrrolo[2,1-c][1,2,4]-benzothiadiazin-7-yl 1-naphthalenecarboxylate Melting point: 248–251° C.

Elemental microanalysis

|  | C % | H % | N % | S % |
|---|---|---|---|---|
| calculated | 63.95 | 4.60 | 7.10 | 8.13 |
| found | 63.69 | 4.54 | 7.03 | 7.91 |

EXAMPLE 20

5,5-Dioxo-2,3,3a,4-tetrahydro-1H-pyrrolo[2,1-c][1,2,4]-benzothiadiazin-7-yl 2-naphthalenecarboxylate Melting point: 207–210 ° C.

Elemental microanalysis

|  | C % | H % | N % | S % |
|---|---|---|---|---|
| calculated | 63.95 | 4.60 | 7.10 | 8.13 |
| found | 64.22 | 4.70 | 7.15 | 7.73 |

EXAMPLE 21

5,5-Dioxo-2,3,3a,4-tetrahydro-1H-pyrrolo[2,1-c][1,2,4]-benzothiadiazin-7-yl [1,1'-biphenyl]-4-carboxylate Melting point: 249–253° C.

Elemental microanalysis

|  | C % | H % | N % | S % |
|---|---|---|---|---|
| calculated | 65.70 | 4.79 | 6.66 | 7.63 |
| found | 65.36 | 4.75 | 6.57 | 7.50 |

EXAMPLE 22

5,5-Dioxo-2,3,3a,4-tetrahydro-1H-pyrrolo[2,1-c][1,2,4]-benzothiadiazin-7-yl phenylacetate Melting point: 169–171° C.

Elemental microanalysis

|  | C % | H % | N % | S % |
|---|---|---|---|---|
| calculated | 60.32 | 5.06 | 7.82 | 8.95 |
| found | 60.56 | 5.00 | 7.54 | 9.16 |

EXAMPLE 23

5,5-Dioxo-2,3,3a,4-tetrahydro-1H-pyrrolo[2,1-c][1,2,4]-benzothiadiazin-7-yl 3-phenyl-2-propenoate Melting point: 193–198° C.

Elemental microanalysis

|  | C % | H % | N % | S % |
|---|---|---|---|---|
| calculated | 61.61 | 4.90 | 7.56 | 8.66 |
| found | 61.81 | 5.00 | 7.21 | 8.56 |

EXAMPLE 24

5,5-Dioxo-2,3,3a,4-tetrahydro-1H-pyrrolo[2,1-c][1,2,4]-benzothiadiazin-7-yl 4-methoxybenzoate Melting point: 216–221° C.

Elemental microanalysis

|  | C % | H % | N % | S % |
|---|---|---|---|---|
| calculated | 57.74 | 4.85 | 7.48 | 8.56 |
| found | 57.05 | 4.77 | 7.39 | 8.48 |

EXAMPLE 25

5,5-Dioxo-2,3,3a,4-tetrahydro-1H-pyrrolo[2,1-c][1,2,4]-benzothiadiazin-7-yl (4-dimethylamino) benzoate Melting point: 232–235° C.

Elemental microanalysis

|  | C % | H % | N % | S % |
|---|---|---|---|---|
| calculated | 58.90 | 5.46 | 10.85 | 8.28 |
| found | 58.83 | 5.48 | 10.76 | 8.43 |

EXAMPLE 26

5,5-Dioxo-2,3,3a,4-tetrahydro-1H-pyrrolo[2,1-c][1,2,4]-benzothiadiazin-7-yl 3-chlorobenzoate Melting point: 243–247° C.

Elemental microanalysis

|  | C % | H % | N % | S % | Cl % |
|---|---|---|---|---|---|
| calculated | 53.9 | 3.99 | 7.39 | 8.46 | 9.36 |
| found | 53.78 | 4.03 | 7.23 | 8.23 | 9.89 |

EXAMPLE 27

5,5-Dioxo-2,3,3a,4-tetrahydro-1H-pyrrolo[2,1-c][1,2,4]-benzothiadiazin-7-yl 4-cyanobenzoate Melting point: 260–264° C.

Elemental microanalysis

|  | C % | H % | N % | S % |
|---|---|---|---|---|
| calculated | 58.53 | 4.09 | 11.38 | 8.68 |
| found | 58.9 | 4.16 | 11.42 | 8.71 |

EXAMPLE 28

5,5-Dioxo-2,3,3a,4-tetrahydro-1H-pyrrolo[2,1-c][1,2,4]-benzothiadiazin-7-yl 4-methylbenzoate Melting point: 198–200° C.

Elemental microanalysis

|  | C % | H % | N % | S % |
|---|---|---|---|---|
| calculated | 60.32 | 5.06 | 7.82 | 8.95 |
| found | 60.36 | 5.09 | 7.67 | 8.57 |

EXAMPLE 29

5,5-Dioxo-2,3,3a,4-tetrahydro-1H-pyrrolo[2,1-c][1,2,4]-benzothiadiazin-7-yl 3-methylbenzoate Melting point: 214–218° C.

Elemental microanalysis

|  | C % | H % | N % | S % |
|---|---|---|---|---|
| calculated | 60.32 | 5.06 | 7.82 | 8.95 |
| found | 60.04 | 5.04 | 7.68 | 8.64 |

EXAMPLE 30

5,5-Dioxo-2,3,3a,4-tetrahydro-1H-pyrrolo[2,1-c][1,2,4]-benzothiadiazin-7-yl 2-methylbenzoate Melting point: 218–221° C.

Elemental microanalysis

|  | C % | H % | N % | S % |
|---|---|---|---|---|
| calculated | 60.32 | 5.06 | 7.82 | 8.95 |
| found | 60.25 | 5.03 | 7.65 | 8.61 |

EXAMPLE 31

5,5-Dioxo-2,3,3a,4-tetrahydro-1H-pyrrolo[2,1-c][1,2,4]-benzothiadiazin-7-yl 3-cyanobenzoate Melting point: 203–206° C.

Elemental microanalysis

|  | C % | H % | N % | S % |
|---|---|---|---|---|
| calculated | 58.53 | 4.09 | 11.38 | 8.68 |
| found | 58.50 | 4.16 | 11.17 | 8.35 |

EXAMPLE 32

5,5-Dioxo-2,3,3a,4-tetrahydro-1H-pyrrolo[2,1-c][1,2,4]-benzothiadiazin-7-yl pentaflurobenzoate Melting point: 205–209° C.

Elemental microanalysis

|  | C % | H % | N % | S % |
|---|---|---|---|---|
| calculated | 47.01 | 2.55 | 6.45 | 7.38 |
| found | 46.95 | 2.56 | 6.33 | 7.05 |

EXAMPLE 33

5,5-Dioxo-2,3,3a,4-tetrahydro-1H-pyrrolo[2,1-c][1,2,4]-benzothiadiazin-7-yl 3-thiophenecarboxylate Melting point: 208–212° C.

Elemental microanalysis

|  | C % | H % | N % | S % |
|---|---|---|---|---|
| calculated | 51.42 | 4.03 | 7.99 | 18.30 |
| found | 51.68 | 4.01 | 8.07 | 17.84 |

EXAMPLE 34

5,5-Dioxo-2,3,3a,4-tetrahydro-1H-pyrrolo[2,1-c][1,2,4]-benzothiadiazin-7-yl 2-thiophenecarboxylate Melting point: 212–214° C.

Elemental microanalysis

|  | C % | H % | N % | S % |
|---|---|---|---|---|
| calculated | 51.42 | 4.03 | 7.99 | 18.30 |
| found | 51.33 | 4.43 | 8.03 | 18.48 |

EXAMPLE 35

5,5-Dioxo-2,3,3a,4-tetrahydro-1H-pyrrolo[2,1-c][1,2,4]-benzothiadiazin-7-yl 3-furancarboxylate Melting point: 185–187° C.

Elemental microanalysis

|  | C % | H % | N % | S % |
|---|---|---|---|---|
| calculated | 53.89 | 4.22 | 8.38 | 9.59 |
| found | 53.89 | 4.22 | 8.36 | 9.52 |

EXAMPLE 36

5,5-Dioxo-2,3,3a,4-tetrahydro-1H-pyrrolo[2,1-c][1,2,4]-benzothiadiazin-7-yl 2-furancarboxylate Melting point: 205–208° C.

Elemental microanalysis

|  | C % | H % | N % | S % |
|---|---|---|---|---|
| calculated | 53.89 | 4.22 | 8.38 | 9.59 |
| found | 53.55 | 4.23 | 8.16 | 9.59 |

EXAMPLE 37

5,5-Dioxo-2,3,3a,4-tetrahydro-1H-pyrrolo[2,1-c][1,2,4]-benzothiadiazin-7-yl nicotinate Melting point: 227–230° C.

Elemental microanalysis

|  | C % | H % | N % | S % |
|---|---|---|---|---|
| calculated | 55.64 | 4.38 | 12.17 | 9.28 |
| found | 55.32 | 4.43 | 11.63 | 9.43 |

EXAMPLE 38

5,5-Dioxo-2,3,3a,4-tetrahydro-1H-pyrrolo[2,1-c][1,2,4]-benzothiadiazin-7-yl 4-pyridinecarboxylate hydrochloride Melting point: 243–247° C.

Elemental microanalysis

|  | C % | H % | N % | S % | Cl % |
|---|---|---|---|---|---|
| calculated | 50.33 | 4.22 | 11.00 | 8.4 | 9.28 |
| found | 50.00 | 4.54 | 10.69 | 8.18 | 8.91 |

EXAMPLE 39

5,5-Dioxo-2,3,3a,4-tetrahydro-1H-pyrrolo[2,1-c][1,2,4]-benzothiadiazin-7-yl 2-pyridinecarboxylate hydrochloride Melting point: 227–230° C.

Elemental microanalysis

|  | C % | H % | N % | S % | Cl % |
|---|---|---|---|---|---|
| calculated | 50.33 | 4.22 | 11.00 | 8.40 | 9.28 |
| found | 50.93 | 4.30 | 10.85 | 8.36 | 7.21 |

Pharmacological Study of the Compounds of the Invention

Study of Excitatory Fluxes Induced by AMPA in *Xenopus oocytes* a—Method:

mRNAs are prepared from cerebral cortex of male Wistar rat by the guanidium thiocyanate/phenol/chloroform method. The poly ($A^+$) mRNAs are isolated by chromatography on oligo-dT cellulose and injected with 50 ng per oocyte. The oocytes are left for 2 to 3 days' incubation at 18° C. to enable expression of the receptors and are then stored at 8–10° C.

Electrophysiological recording is carried out in a Plexiglass® chamber at 20–24° C. in an OR2 medium (J. Exp. Zool., 1973, 184, 321–334) by the 2-electrode "voltage-clamp" method, with a 3rd electrode being placed in the bath to serve as reference.

All the compounds are administered via the incubation medium and the electric current is measured at the end of the period of administration. AMPA is used in a concentration of 10 μM. For each compound studied, there is determined the concentration that doubles (EC2X) or quintuples (EC5X) the intensity of the flux induced by AMPA alone (5 to 50 nA).

b—Results:

The compounds of the invention potentiate the excitatory effects of AMPA very considerably and their activity is very clearly superior to that of the reference compounds.

| Compound | EC2X (μM) |
|---|---|
| Ex. 1 | 12 |
| Ex. 4 | 35 |
| Ex. 7 | 34 |
| Ex. 8 | 20 |
| Ex. 9 | 296 |
| Ex. 10 | 14 |
| Ex. 11 | 5 |
| Ex. 28 | 3.6 |
| Ex. 34 | 1.3 |
| Ex. 36 | 2.0 |
| Ex. 37 | 4.0 |

Pharmaceutical Composition

| Formulation for the preparation of 1000 tablets each containing a dose of 100 mg | |
|---|---|
| Compound of Example 1 | 100 g |
| Hydroxypropylcellulose | 2 g |
| Wheat starch | 10 g |
| Lactose | 100 g |
| Magnesium stearate | 3 g |
| Talcum | 3 g |

We claim:

1. A compound of formula (I):

(I)

wherein:
$R_1$ represents hydroxy, RCO—O— or RCO—$NR_a$—,
$R_2$ represents hydrogen, halogen, or hydroxy, R'CO—O or R'CO—$NR'_a$—,
R and R', which may be identical or different, represent linear or branched ($C_1$–$C_6$)alkyl optionally substituted by aryl, linear or branched ($C_2$–$C_6$)alkenyl optionally substituted by aryl, linear or branched ($C_1$–$C_6$) perhaloalkyl, ($C_3$–$C_7$)cycloalkyl, adamantyl, aryl or heteroaryl,
$R_a$ and $R'_a$, which may be identical or different, represent hydrogen or linear or branched ($C_1$–$C_6$)alkyl, linear or branched ($C_1$–$C_6$)perhaloalkyl, linear or branched ($C_1$–$C_6$)acyl, aryl or heteroaryl, its isomers and addition salts thereof with a pharmaceutically acceptable acid or base, it being understood that:
"aryl group" is understood to mean a monocyclic aromatic group, or a bicyclic group in which at least one of the rings is aromatic, wherein the aryl group is selected from phenyl, naphthyl, and tetrahydronaphthyl, which groups are optionally substituted by one or more, identical or different, groups selected from halogen, linear or branched ($C_1$–$C_6$)alkyl, linear or branched ($C_1$–$C_6$)alkoxy, linear or branched ($C_1$–$C_6$)perhaloalkyl, linear or branched ($C_1$–$C_6$)perhaloalkoxy, hydroxy, cyano, nitro, amino (optionally substituted by one or more linear or branched ($C_1$–$C_6$)alkyl groups), aminosulphonyl (optionally substituted by one or more linear or branched ($C_1$–$C_6$)alkyl groups) and phenyl (optionally substituted by one or more, identical or different, groups selected from halogen, linear or branched ($C_1$–$C_6$)alkyl, linear or branched ($C_1$–$C_6$) perhaloalkyl, hydroxy and linear or branched ($C_1$–$C_6$)alkoxy), "heteroaryl group" is understood to mean a monocyclic aromatic group, or a bicyclic group in which at least one of the rings is aromatic, wherein the heteroaryl group is selected from pyridyl, pyrrolyl, thienyl, furyl, imidazolyl, and indolyl, which groups contain one, two or three identical or different hetero atoms selected from nitrogen, oxygen and sulphur, and are optionally substituted by one or more, identical or different, groups selected from halogen, linear or branched ($C_1$–$C_6$)alkyl, linear or branched ($C_1$–$C_6$) alkoxy, linear or branched ($C_1$–$C_6$)perhaloalkyl, linear or branched ($C_1$–$C_6$)perhaloalkoxy, hydroxy, cyano, nitro, amino (optionally substituted by one or more linear or branched ($C_1$–$C_6$)-alkyl groups) and aminosulphonyl (optionally substituted by one or more linear or branched ($C_1$–$C_6$)alkyl groups).

2. A compound of claim 1, wherein $R_1$ represents hydroxy and $R_2$ represents hydrogen or halogen.

3. A compound of claim 1, wherein $R_1$ represents RCO—O— and $R_2$ represents hydrogen.

4. A compound of claim 3, wherein R represents ($C_3$–$C_7$) cycloalkyl, aryl or heteroaryl.

5. The compound of claim 1 selected from:
5,5-dioxo-2,3,3a,4-tetrahydro-1H-pyrrolo[2,1-c][1,2,4] benzothiadiazin-7-ol,
5,5-dioxo-2,3,3a,4-tetrahydro-1H-pyrrolo[2,1-c][1,2,4] benzothiadiazin-7-yl benzoate,
5,5-dioxo-2,3,3a,4-tetrahydro-1H-pyrrolo[2,1-c][1,2,4] benzothiadiazin-7-yl cyclohexanecarboxylate,
5,5-dioxo-2,3,3a,4-tetrahydro-1H-pyrrolo[2,1-c][1,2,4] benzothiadiazin-7-yl cyclobutanecarboxylate,
5,5-dioxo-2,3,3a,4-tetrahydro-1H-pyrrolo[2,1-c][1,2,4] benzothiadiazin-7-yl 4-methylbenzoate,
5,5-dioxo-2,3,3a,4-tetrahydro-1H-pyrrolo[2,1-c][1,2,4] benzothiadiazin-7-yl 3-thiophenecarboxylate,
5,5-dioxo-2,3,3a,4-tetrahydro-1H-pyrrolo[2,1-c][1,2,4] benzothiadiazin-7-yl 2-thiophenecarboxylate,
5,5-dioxo-2,3,3a,4-tetrahydro-1H-pyrrolo[2,1-c][1,2,4] benzothiadiazin-7-yl 3-furan-carboxylate,
5,5-dioxo-2,3,3a,4-tetrahydro-1H-pyrrolo[2,1-c][1,2,4] benzothiadiazin-7-yl 2-furan-carboxylate, and 5,5-dioxo-2,3,3a,4-tetrahydro-1H-pyrrolo[2,1-c][1,2,4]benzothiadiazin-7-yl nicotinate.

6. A method for promoting memory enhancement in an animal or human living body comprising the step of administering to the animal or human living body an amount of a compound of claim 1 that is effective for such purpose.

7. A pharmaceutical composition comprising as active principle an effective amount of a compound as claimed in claim 1, together with one or more pharmaceutical acceptable excipients or vehicles.

* * * * *